United States Patent [19]

Pasarela

[11] 4,343,790
[45] Aug. 10, 1982

[54] CONTROLLED RELEASE ACRYLIC POLYMER COATED GRANULAR PESTICIDAL COMPOSITIONS WITH ATTENDANT REDUCED DERMAL TOXICITY

[75] Inventor: Nunzio R. Pasarela, Bridgewater, N.J.

[73] Assignee: American Cyanamid Company, Stamford, Conn.

[21] Appl. No.: 174,951

[22] Filed: Aug. 4, 1980

Related U.S. Application Data

[63] Continuation of Ser. No. 9,883, Feb. 6, 1979, abandoned.

[51] Int. Cl.³ .................... A01N 25/10; A01N 57/00; A01N 25/00; A61K 31/78
[52] U.S. Cl. ........................................ 424/81; 424/32; 424/202; 424/216; 424/357
[58] Field of Search ................... 424/216, 202, 32, 81, 424/357

[56] References Cited

U.S. PATENT DOCUMENTS

| | | | |
|---|---|---|---|
| 3,400,093 | 9/1968 | Feinberg | 424/81 |
| 3,691,090 | 9/1972 | Kitagima et al. | 424/32 |
| 3,909,444 | 9/1975 | Anderson et al. | 424/32 |
| 4,059,700 | 11/1977 | Lindsay | 424/216 |
| 4,061,740 | 12/1977 | Boatright | 424/202 |
| 4,065,558 | 12/1977 | Gordon | 424/216 |
| 4,107,292 | 8/1978 | Nemeth | 424/32 |

OTHER PUBLICATIONS

Chem. Abst. 86 63487(e) (1977)—Chen.

*Primary Examiner*—Douglas W. Robinson
*Attorney, Agent, or Firm*—H. G. Jackson

[57] ABSTRACT

There are provided pesticidal compositions of low mammalian dermal toxicity comprising granular carriers impregnated or coated with a phosphorus containing pesticide, such as 2-diethoxyphosphinylimino)-1,3-dithiolane, 2-(diethoxyphosphinylimino)-4-methyl-1,3-dithiolane, 2-(diethoxyphosphinylimino)-1,3-dithietane, O,O-diethyl S-(ethylthiomethyl)phosphorodithioate and O,O-diethyl S-{[(1,1-dimethylethyl)thio]methyl}-phosphorodithioate, and any equivalent thereof, and further coated with an acrylic polymer, and methods for preparing same. Furthermore, there are provided compositions which will release toxicant into the surrounding environment either over a relatively short period of time in a controlled fashion or over a prolonged period of time.

9 Claims, No Drawings

CONTROLLED RELEASE ACRYLIC POLYMER COATED GRANULAR PESTICIDAL COMPOSITIONS WITH ATTENDANT REDUCED DERMAL TOXICITY

This is a continuation of application Ser. No. 9,883, filed Feb. 6, 1979, now abandoned.

SUMMARY OF THE INVENTION

It is known that a number of phosphorus pesticidal compounds, such as 2-(diethoxyphosphinylimino)-1,3-dithiolane, 2-(diethoxyphosphinylimino)-4-methyl-1,3-dithiolane, 2-(diethoxyphosphinylimino)-1,3-dithietane, O,Odiethyl S-(ethylthiomethyl)phosphorodithioate and O,O-diethyl S-(ethylthiomethyl)phosphorodithioate and phorodithioate, are highly effective for the control of broad spectrum of insects and/or nematodes which attack and destroy agriculturally imported food and fodder crops. It is, therefore, of advantage to utilize such compounds in various compositions useful in agriculture. Unfortunately, these otherwise highly effective pesticides are extremely toxic when introduced into the human circulatory system as by ingestion, inhalation, or dermal absorption.

Thus, the use of compositions containing the above referred-to compounds for the control of insect pests represents a distinct hazard to indivuals engaged in the use and application thereof. Similar hazards are encountered by those who are engaged in storing, transporting and distributing to the ultimate user such compositions.

Practical use aspects of the above referred-to pesticide compounds for intended pest control often dictate the use of various granular carrier compositions in which the pesticidal compound is adsorbed or absorbed onto or into the carrier composition. These granular carrier compositions not only provide a more dilute composition of the active pesticide for appropriate applications in agronomic uses but also serve to reduce the potential hazard in use of the pesticide through dermal absorption. Even though such formulated compositions tend to reduce the potential hazard of dermal absorption of the above referred-to pesticides, it is highly desirable to reduce the potential hazard even more.

It is, therefore, a principal object of the invention to provide granular formulation compositions containing the aforementioned pesticides having low mammalian dermal toxicity while fully retaining their effectiveness. It is a further object to provide compositions which would offer a margin of safety otherwise not found in conventional compositions containing such pesticides. Other objects and advantages will become apparent from a reading of the ensuing description.

To these ends, it has been found that, when solid granular compositions containing the aforementioned pesticides are treated as by spraying, for instance, with certain acrylic latices, or with solutions of certain acrylic polymers in organic solvents, the resultant acrylic polymer coated compositions possess advantageously a two to three fold margin of safety due to their lowered mammalian dermal toxicity as compared to similar, uncoated compositions, while their pesticidal activity and physical integrity remains unchanged. These effects are accomplished in a straightforward manner by applying certain acrylic latex compositions or solutions of certain polymers in an organic solvent to the surfaces of said impregnated pesticidal granules.

According to the process of the invention, the compositions of the granular formulation, prior to acrylic polymer coating, are prepared by impregnating a toxicant ranging from about 2% to about 25%, by weight, and preferably, from 2.5% to 20%, by weight, said toxicant being 2-(diethoxyphosphinylimino)-1,3-dithiolane, 2-(diethoxyphosphinylimino)-4-methyl-1,3-dithiolane 2-(diethoxyphosphinylimino)-1,3-dithietane, O,O-diethyl S-(ethylthiomethyl)phosphorodithioate, O,O-diethyl S-{[(1,1-dimethylethyl)thio]methyl}phosphorodithioate, and equivalents thereof, with a suitable granular carrier. Illustrative of the latter carrier is either (a) a sorptive material, such as attapulgite or montmorillonite (clays), brick chips, pumice, talc, volcanic cinders, corncob grits, or (b) a non-sorptive material, such as sand or limestone chips. If a sorptive material is selected, a deactivator such as ethylene glycol, di-, tri or tetraethylene glycol and mixtures thereof can be added to neutralize intrinsic acidity in amounts ranging from about 3% to about 6%, by weight, of said compositions. In this event, the amount of granular carrier is decreased by an amount equal to that of the deactivator added to said composition. Advantageously, the above described granular composition may be blended and/or coated with from about 0.5%, by weight, to about 2%, by weight, of composition of a finely divided sorptive substrate, such as calcined powdered clays, diatomaceous earth, calcium silicate, fumed silica, and fumed silica which has been made hydrophobic by the replacement of most of the hydrophilic hydroxyl group, which normally populate the silica surface, with trimethylsiloxyl groups as well as mixtures of said substrate. It has been found that the addition of said sorptive substrate to the granular formulations aids in maintaining the free-flow formation of agglomerates in same particularly subsequent to treatment with a sprayed acrylic polymer, defined hereinbelow with particularity.

It is a good practice to coat impregnated granular formulations, hereinabove set forth by any suitable means, such as by spraying with an acrylic latex. The coating is accomplished by spraying either an aqueous emulsion of an acrylic polymer or a solution of an appropriate acrylic polymer in amounts sufficent to provide an acrylic polymer coating of from about 0.5% to about 5%, by weight, and, preferably, from about 1.5% to about 4%, by weight, of the overall granular formulation. Examplary of the above mentioned acrylic latices are (a) thermoplastic acrylic emulsion polymers with a solids content of from about 38% to about 43%, by weight, and having an intrinsic viscosity range of from 0.75 to 3.1 dl/g at 30° C. in THF (tetrahydrofuran), (b) crosslinking acrylic emulsion polymers with a solids content of about 45-46%, by weight, and having an intrinsic viscosity range of from 1.0 to 2.0 and, preferably, about 1.4 dl/g at 30° C. in DMF (dimethylformamide), and (c) solutions of acrylic polymers in tetrahydrofurfuryl alcohol, wherein said acrylic polymers have an intrinsic viscosity range of from about 0.05 to 0.1 dl/g and, preferably, about 0.085 dl/g at 30° C. in butanol.

It is an advantage of the process of the invention to prepare the coated granular compositions in a straightforward manner involving a plurality of steps. From about 2% to about 30%, by weight, and preferably from about, 2.5% to about 20%, by weight, of formulation of a toxicant selected from the above identified group, for instance, O,O-diethyl S-{[(1,1-dimethylethyl)thio[methyl}phosphorodithioate, is mixed with from about 3% to about 6%, by weight, of formulation of a deactivator selected from the group consisting of ethylene glycol, di-, tri- or tetraethylene glycol and mixtures thereof. The weight percent of the overall mixture is based on the weight of the carrier. This mixture is then sprayed on a granular carrier selected from the group consisting of clays, such as attapulgite and montmorillonite clays, brick chips, pumice, talc, volcanic cinders, corncob grits, sand and limestone chips, wherein said carrier is used in amounts from about 62%, by weight, to about 94% and, preferably, from about 68% to about 92%, by weight, of formulation. After the spraying has been completed, agitation of the mixture is continued until all of the liquid is absorbed. Thereafter, if so desired, from about 0.5% to about 2%, by weight, of a finely divided sorptive substrate is added and agitation of the mixture continued until a uniform blend is obtained. The latter sorptive substrate is illustrative calcined powdered clays, diatomaceous earth, calcium silicate, fumed silica and fumed silica which has been made hydrophobic as by the replacement of most of the hydrophilic hydroxyl groups which normally populate the silica surface with trimethylsiloxy groups. The formulations so-prepared are then agitated by suitable means and sprayed with either one of a group of certain acrylic latices (an aqueous emulsion of an acrylic polymer) or a solution of said acrylic polymer in a solvent, such as tetrahydrofurfuryl alcohol, in amounts sufficient to provide an acrylic polymer coating of from about 0.5% to about 5%, by weight, and, preferably, from about 1.5% to about 4%, by weight, of said granular formulations. The latter latices are selected from hard thermoplastic acrylic emulsion polymers with a solids content ranging from about 38% to about 43%, by weight, and having an intrinsic viscosity range of from 0.75 to 3.1 dl/g at 30° C. in THF (tetrahydrofuran), from hard self-crosslinking acrylic emulsion polymers with a solids content of about 45-46%, by weight, and having an intrinsic viscosity range of from 1.0 to 2.0 and, preferably, about 1.4 dl/g at 30° C. in dimethylformamide (DMF), and from solutions of acrylic polymers in tetrahydrofurfuryl alcohol, wherein said acrylic polymers have an intrinsic viscosity range of from 0.05 to 0.1 dl/g and, preferably, 0.085 dl/g at 30° C. in butanol. If desired, the above formulations may be heated to accelerate and increase the hardening of said coatings.

It is found that, by utilizing the method of the present invention employing the above identified compounds in the combinations and percent weight ranges given above, a number of compositions can be prepared within which it is possible to select one wherein the toxicant is released rapidly into the surrounding environment over a relatively short period of time; or to alternatively select a composition which will release said toxicant slowly over a prolonged period of time. Thus, it is possible to adjust within certain practical limits, if so desired, the controlled release of toxicant from the novel compositions of the present invention by the selection of suitable formulations.

The coated granular pesticidal compositions also so shown reduced mammalian dermal toxicity.

The present invention is further illustrated by the following examples which are not to be taken as being limitative thereof. Unless otherwise stated, the percentages set forth are by weight.

EXAMPLE 1

Preparation of a granular formulation containing 15% by weight of O,O-diethyl S-{[(1,1-dimethylethyl)thio]methyl}phosphorodithioate A. 78.5 gms. of granular (25/50) montmorillonite having the composition set forth below are charged to a rotating type blender and agitated. While being agitated, the granules are sprayed with a mixture of the insecticide: O,O-diethyl S-{[(1,1-dimethylethyl)thio]methyl}phosphorodithioate (17.5 gms. 88.57% real=15.5 g. real) and a deactivator comprising a mixture of ethylene, di-, tri- and tetraethylene glycol, (4.0 gms.)

After the spraying has been completed, blending is continued until all the liquid is absorbed. There is obtained 100 gms. of a granular formulation containing 1.5 w/w of the above insecticide.

| Montmorillonite Analysis | |
|---|---|
| Component | % by weight, range |
| Silica (SiO$_2$) | 68-72.5 |
| Ferric oxide (Fe$_2$O$_3$) | 5-7 |
| Aluminum oxide (Al$_2$O$_3$) | 11-15 |
| Calcium oxide (CaO) | 0.012-1.5 |
| Magnesium oxide (MgO) | 0.8-1.6 |
| Sodium oxide (Na$_2$O) | 0.08-0.4 |
| Potassium oxide (K$_2$O) | 1.1-1.6 |
| Phosphoric acid (P$_2$O$_5$) | 0.1-0.2 |
| Cr, Cu, Mn, Ni, Ti | trace |
| Ignition loss | 3-7.5 |

B. Following above method, but substituting 78.5 gms. of attapulgite having the analysis set forth below, containing 15.5 w/w of the above insecticide is prepared.

| Attapulgite Analysis | |
|---|---|
| Component | % by weight |
| Silica | 64.37 |
| Aluminum | 12.46 |
| Ferric oxide | 5.93 |
| Magnesium oxide | 5.28 |
| Calcium oxide | 0.99 |
| Sodium oxide | 0.05 |
| Potassium oxide | 1.58 |
| Titanium dioxide | 0.73 |
| Loss on ignition | 8.21 |

EXAMPLE 2

Preparation of acrylic polymer coated granular pesticidal formulations a. A granular insecticidal formulation (100 g) prepared by the method of Example 1A above is tumbled in a rotating type blender and sprayed with a hard, thermoplastic acrylic emulsion polymer with a solids content of 38% and with an intrinsic velocity of 3.1dl/g at 30° C. in THF (10 ml of latex is used). There is obtained 110 g of free-flowing and dry granules containing 14.09%, by weight, of toxicant.

b. A sample of the above formulation is stored at 45° C. for 2 hours.

c. A granular insecticidal formulation (100 g) prepared by the method of Example 1A above is sprayed as above with a mixture of a hard thermoplastic acrylic emulsion polymer, solids content 43%, by weight, and with an intrinsic viscosity of 0.75 dl/g at 30° C. in THF and dibutyl phthalate (6 ml of a 60:40 mixture). There is obtained 106 g of formulation containing 14.6% by weight of toxicant.

By the methods of a, b and c above, granular formulations are prepared, containing 15.5%, by weight, or 20.5%, by weight, of O,O-diethyl S-{[(1,1-dimethylethyl)thio]methyl}phosphorodithioate, respectively.

EXAMPLE 3

Preparation of acrylic polymer coated granular pesticidal formulations

Procedure

A granular insecticidal formulation (100 g) prepared by the method of Example 1A, above and a finely divided hydrophobic silica (0.5 g; 0.5%) in which most of the surface hydroxyl groups have been replaced by trimethylsiloxyl groups, are mixed and blended for 5 minutes prior to being sprayed with the respective coatings.

a. A granular formulation (100.5 g) prepared by the above procedure is agitated and sprayed with a hard self-crosslinking acrylic emulsion polymer with a solids content of 45%, by weight, and with an intrinsic viscosity of 1.4 dl/g at 30° C. in DMF (4 ml of latex used for coating). The thus obtained formulation (104.5 g; 14.83% real) is free-flowing, dry, and shows no tendency to form agglomerates;

b. The procedure of a above is followed except that 6 ml of latex are used to coat the granules (106.5 g; 14.55% real); or c. A granular formulation (100.5 g) prepared by the above procedure is agitated and sprayed with a hard self-crosslinking acrylic emulsion polymer with a solids content of 45%, by weight, and with an intrinsic ciscosity of 1.4 dl/g at 30° C. in DMF (6 ml of latex used for coating). The thus obtained formulation (106.5 g; 14.55% real) is free-flowing, dry, and shows the presence of only trace amount of agglomerates.

By the methods of a, b or c above, a granular formulation is prepared which contains 15.5%, by weight, or 20.5%, by weight, of O,O-diethyl S-{[(1,1-dimethylethyl)thio]methylphosphorodithioate, respectively.

EXAMPLE 4

Preparation of acrylic polymer coated granular pesticidal formulation

Procedure

A granular insecticidal formulation (100 g) prepared by the method of Example 1A, above, and a finely divided hydrophobic silica in which most of the surface hydroxyl groups have been replaced by trimethylsiloxyl groups (1.0 g; 1%) are blended for 5 minutes prior to being sprayed with the respective coatings.

a. A granular formulation (101 g) prepared by the above procedure is tumbled in a rotating type of blender and sprayed with a hard, self-crosslinking acrylic emulsion polymer with a solids content of 45%, by weight, and with an intrinsic viscosity of 1.4 dl/g at 30° C. in DMF (4 ml of latex used). The thus obtained composition (105 g; 14.76% real) is free-flowing, dry, and shows no tendency to form agglomerates;

b. A granular formulation (101 g) prepared by the above procedure is tumbled and sprayed with a hard, self-crosslinking acrylic emulsion polymer with a solids content of 45%, by weight, and with an intrinsic viscosity of 1.4 dl/g at 30° C. in DMF (6 ml of latex used). The thus obtained composition (107 g; 14.48% real) is free-flowing, dry, and does not form aggregates.

EXAMPLE 5

Preparation of acrylic polymer coated granular pesticidal formulations

Procedure

There are admixed 100 gms of a granular insecticidal formulation prepared by the method of Example 1A, above, together with 0.5 gm of a finely divided hydrophobic silica in which most of the surface hydroxyl groups have been replaced by trimethylsiloxyl groups. The admixing takes place within 5 minutes prior to being sprayed with the respective coatings.

a. A granular formulation (100.5 g) prepared by the above procedure is agitated and sprayed with a hard thermoplastic acrylic emulsion polymer with a solids content of 43%, by weight, and with an intrinsic viscosity of 0.75 dl/g at 30° C. in THF (6 ml of latex used). The thus obtained composition (106.5 g; 14.55% real) is dry and forms only a few agglomerates.

b. As under a except that 1.0 g (1%) of the above hydrophobic silica is used in the formulation. The thus-obtained composition (107 g; 14.48% real) is dry and forms no agglomerates.

EXAMPLE 6

Preparation of a granular formulation containing 20% by weight of O,O-diethyl S-{[(1,1-dimethylethyl)thio]methyl}phosphorodithioate Granular (25/50) montmorillonite clay (66.2 g) is agitated in a blender and while being agitated, the granules are sprayed with a mixture of O,O-diethyl-S-{[(1,1-dimethylethyl)thio]methyl}phosphorodithioate (22.8 g; 90.38% real=20.6 g real) and a deactivator comprising a mixture of ethylene, di-, tri- and tetraethylene glycol (4.0 g). After the spraying step has been completed, finely divided hydrophobic silica in which most of the surface hydroxyl groups have been replaced by trimethylsiloxyl groups (1.0 g; 1%) is added and blending is continued for 5 minutes. The thus-obtained blend is tumbled and spayed with a hard, self-crosslinking acrylic emulsion polymer with a solids content of 45% by weight and with intrinsic viscosity of 1.4 dl/g at 30° C. in DMF (6 ml of latex used). The composition is free-flowing and dry.

EXAMPLE 7

Preparation of a granular formulation containing 10% by weight of O,O-diethyl S-(ethylthiomethyl)phosphorodithioate a. Brick chips (79.07 g) are charged to a rotating type blender. While being agitated, the chips are sprayed with the insecticide: O,O-diethyl S-(ethylthiomethyl)-phosphorodithioate (11.93 g of 88% real=10.5 g real, and diethylene glycol (5.0 g). Next, the so-treated chips are sprayed with a 37.5% w/w solution of an acrylic polymer in tetrahydrofurfuryl alcohol (4.0 g) to provide a polymer coating for said chips. The acrylic polymer is characterized by having an intrinsic viscosity of 0.085 dl/g at 30° C. in butanol. There is obtained 100 g of a granular formulation containing 10% w/w of the above insecticide (with a 5% overage).

The above formulation has an $LD_{50}$ of >200 mg/kg by the method of Example 9, whereas a similar, but uncoated, sample has an $LD_{50}$ of 110 mg/kg.

b. By the method of a, but substituting O,O-diethyl S-{[(1,1-dimethylethyl)thio]methyl}phosphorothioate (10.5 g real) for the above insecticide, a granular formulation can be prepared.

c. The preparation under a is repeated except that the sprayed brick chips are blended for 5 minutes with 0.5%, by weight, of a finely divided hydrophobic silica in which most of the surface hydroxyl groups have been replaced by trimethylsiloxyl groups, and the thus prepared blend is then sprayed with a hard thermoplastic acrylic emulsion polymer with a solids content of 38% and with an intrinsic viscosity of 3.1 g dl/g at 30° C. in THF, to provide 1.9%, by weight, of formulation of said polymers.

The thus obtained composition has a dermal $LD_{50}$ of from >120 to <200 mg/kg by the method of Example 9.

The properties of the acrylic resins employed in the above Examples 2a, 2b and 7c, for instance, are further characterized below. The resins, manufactured by the Rohm and Hass Co. is sold under the trademark, RHOPLEX ® B-85. It has the following typical physical properties:

| | |
|---|---|
| Appearance | White milky liquid |
| Solids | 38.0 ± 0.5 percent |
| pH (as shipped) | 9.5 to 10.0 |
| Weight per gallon | 8.9 lbs. |
| Dry bulking value (gal/lb.) | 0.102 (calculated) |
| Tukon hardness (KHN) | 18 |
| Colloidal charge | Anionic |
| Minimum film-formulation temperature | >90° C. |

In Examples 2c, 5a and 5b, above, the acrylic resin is manufactured by Rohm and Haas Co. and is sold under the trademark RHOPLEX ® B-88. It has the following typical physical properties:

| | |
|---|---|
| Appearance | White milky liquid |
| Solids content | 42 to 43% |
| Viscosity | Less than 100 cps. |
| pH (as shipped) | 8.5 to 9.0 |
| Ionic nature | Nonionic |
| Minimum film-forming temperature | Greater than 90° C. |
| Tukon hardness (approx.) | 18 KHN |

In Examples 3a, 3b and 4a, above, the acrylic resin manufactured by the Union Carbide Co. and is sold under the trademark UCAR ® Latex 189. It has the following typical physical properties:

| | |
|---|---|
| Polymer Type | Hard, self-crosslinking acrylic |
| Emulsifier | Anionic |
| Total solids | 45% by wt. |
| Viscosity (Brookfield, Model LVT, Spindle No. 2,60 rpm) | <100cp |
| pH at 25° C. | 4.0 |
| Apparent Specific Gravity at 20/20° C. | 1.07 |
| Weight per Gallon at 20° C. | 8.9 lb |
| Particle Size (microns) | 0.3 |
| Surface Tension (dynes per cm.) | 38 |

In Examples 3c, 4b and 6, above, the acrylic resin is manufactured by the Union Carbide Co. and is sold under the UCAR ® Latex 879. It has the following typical physical properties:

| | |
|---|---|
| Total Solids, % by weight | 46 |
| Brookfield Viscosity (maximum), Model LVT, Spindle No. | |
| 1,60 rpm., cps | 100 |
| pH at 25° C. | 4.5 |
| Apparent Specific Gravity at 20/20° C. | 1.07 |
| Weight per Gallon at 20° C. | 8.90 |
| Surface Tension, dynes per cm. at 30% total solids | 50 |

In Example 7a and 7b, the acrylic resin is manufactured by the American Cyanamid Co. and is designated as XG4011 Acrylic Resin as having the following typical physical properties:

| | |
|---|---|
| Appearance | Clear, viscous liquid |
| Solids, % by weight | 75 ± 2 |
| Solids, % by volume | 70 ± 2 |
| Solvent | N-Butanol |
| Viscosity, Gardner-Holdt, 25° C. | $Z_5Z_7$ |
| Color, Gardner, 1963, maximum | 1 |
| Acid number, (resin solids) | 100–120 |
| Pounds per gallon, approximate | 8.5 |
| Flash point (Tag Open Cup) | >172° F. |
| Intrinsic Viscosity in Butanol at 30° C. | .085 |

EXAMPLE 8

General method for the evaluation of dermal toxicity of the formulations of the present invention using male albino rabbits as the test animals Materials a. Five male albino rabbits weighing approximately 2.2 to 3.5 kilogram are selected for each dosage level. The hair is shaved from the entire trunk.

b. Saran tubing or "Vinylite" film VU1900, 30.5 cm (12") wide, 0.04 millimeter in thickness and long enough to fit around the rabbit.

c. One felt cloth bandage measuring approximately 22.9×45.7 cm (9"×18").

d. Four pieces of 3.8 cm (1.5") adhesive tape approximately 35.6 cm (14") long.

Procedure a. The granular material is placed in the center of the plastic film and is moistened with water.

b. The rabbits underside is moistened with water and the animals are placed belly down on the material.

c. The plastic is then brought up and around the animal and secured at each end with strips of adhesive tape. The felt cloth is then placed under the belly and brought up around the animal and secured to the body with the remaining two strips of adhesive tape.

Evaluation

Twenty-four hours after dosing, the "cuff" is removed and any remaining material is brushed away. If the test material cannot be removed, the animal is fitted with a fiber collar which prevents the animal from licking the treatment area. The animals are observed for 14 days, post dosing, noting signs of toxicity, skin irritation and mortality. At the end of 14 days, the animals are sacrificed and weighed.

From the data thus obtained, the dermal $LD_{50}$ values (mg/kg body weight) are calculated for the formulations (compositions) of Examples 2 to 6, and are summarized in Table I below, along with the $LD_{50}$ value of the toxicant itself and a granular (non-coated) formulation thereof.

TABLE I

Dermal toxicity of coated granular compositions containing O,O-diethyl S-{[(1,1-dimethylethyl)thio]methyl)phosphorodithioate.

| Composition | $LD_{50}$ mg/kg |
|---|---|
| O,O-diethyl S-{[(1,1-dimethylethyl)thio]methyl}phosphorodithioate (technical) | 1–2 |
| Non-coated, granular; 15% toxicant. | <20 |
| Example 2a | >80 |
| Example 2b | >80 |
| Example 2c | <80>40 |
| Example 3a | >80 |
| Example 3b | >80 |
| Example 4a | >80 |
| Example 4b | >80 |
| Example 5a | <80>40 |
| Example 5b | <80<40 |
| Example 6 | <80>40 |

It can be seen from Table I above, that the coated granular compositions of the present invention are at least two to three-fold less toxic as are the comparable non-coated compositions.

EXAMPLE 9

Southern corn rootworm soil residual test

One quart (950 ml) of moist (about 25% of moisture holding capacity) potting soil is placed in a stainless steel beaker approximately 22 cm deep × 18 cm diameter. A weighed amount of granular is distributed over the soil. The beaker is then capped and rotated on a mechanical mixer for 2 minutes (60 revolutions). Two 1-ounce (29.7 ml) jars of soil are removed for 0 days mortality evaluation with southern corn rootworm (*Diabrotica undecipunctata howardi*) larvae. The remainder of the treated soil is divided between 2 wide-mouth pint (475 ml) treated paper containers. Each container of soil received 100 ml of tap water, bringing the soil to near field moisture holding capacity. A regime of moistening and drying continues throughout the test period. The treated soils plus the untreated control are held in the holding room at about 26.7° C. At weekly intervals the duplicate containers of soil are removed, the soil thoroughly mixed, moistened to about 25% moisture holding capacity, and two 1-ounce (29.7 ml) jars of soil are removed for bioassay with southern corn rootworm larvae.

The data obtained are summarized in Table II below.

TABLE II

Evaluation of the soil residual activity of polymer coated pesticidal granules, containing 15% by weight of O,O-diethyl S-{[(dimethylethyl)thio]methyl}phosphorodithioate against southern corn rootworm larvae.

| Example | Concentration mg. a.i/ 950 ml** soil | Residual Activity (average of two replicates) Percent kill, days past start of week | | | | | | |
|---|---|---|---|---|---|---|---|---|
| | | 0 | 7 | 21 | 42* | 70 | 91 | 131 |
| control | — | 0 | 0 | 30 | 5 | 0 | 0 | 0 |
| uncoated | 1 | 50 | 100 | 100 | 100 | 30 | 0 | 0 |
| | 2 | 100 | 100 | 100 | 100 | 100 | 67 | 0 |
| | 4 | 100 | 100 | 100 | 100 | 100 | 100 | 100 |
| 2a | 1 | 100 | 100 | 100 | 100 | 100 | 44 | 0 |
| | 2 | 100 | 100 | 100 | 100 | 100 | 78 | 0 |
| | 4 | 100 | 100 | 100 | 100 | 100 | 100 | 50 |
| 3a | 1 | 20 | 100 | 100 | 95 | 10 | 0 | 0 |
| | 2 | 90 | 100 | 100 | 100 | 90 | 44 | 0 |
| | 4 | 100 | 100 | 100 | 100 | 100 | 100 | 17 |
| 3b | 1 | 50 | 100 | 100 | 100 | 100 | 67 | 0 |
| | 2 | 70 | 100 | 100 | 100 | 100 | 100 | 0 |
| | 4 | 80 | 100 | 100 | 100 | 100 | 100 | 83 |
| 3c | 1 | 85 | 100 | 100 | 100 | 100 | 11 | 0 |
| | 2 | 80 | 100 | 100 | 100 | 100 | 78 | 0 |
| | 4 | 100 | 100 | 100 | 100 | 100 | 100 | 100 |
| 4a | 1 | 85 | 100 | 100 | 100 | 90 | 0 | 0 |
| | 2 | 100 | 100 | 100 | 100 | 100 | 56 | 0 |
| | 4 | 100 | 100 | 100 | 100 | 100 | 100 | 83 |
| 4b | 1 | 100 | 100 | 100 | 100 | 70 | 0 | 0 |
| | 2 | 100 | 100 | 100 | 100 | 100 | 67 | 0 |
| | 4 | 100 | 100 | 100 | 100 | 100 | 100 | 83 |
| 5a | 1 | 45 | 100 | 100 | 100 | 40 | 22 | 0 |
| | 2 | 75 | 100 | 100 | 100 | 70 | 11 | 0 |
| | 4 | 100 | 100 | 100 | 100 | 100 | 100 | 50 |

*After this day only single tests are run.
**Corresponds to 1.12, 2.24 and 4.48 kg/ha, respectively Advantageously, from the biological data presented in Table II above, it can be seen that certain of the coated granular formulations may be utilized to provide short term controlled release of toxicant, especially at the lower rates applied (e.g. 3a, 4b and 5a; at 1 mg. a.i., 6 to 10 weeks); while others provide long term controlled release of toxicant, especially at the higher rates applied (e.g. 3b, 3c, 4a and 4b; at 4 mg. a.i., 13–19 weeks).

We claim:

1. A solid particulate composition comprising particles of an inert sorptive or non-sorptive granular carrier impregnated or coated with a pesticidally effective amount of a phosphorus pesticide which is O,O-diethyl-S-(ethylthio)methylphosphorodithioate or O,O-diethyl-S-{[(1,1-dimethylethyl)thio]methyl} phosphorodithioate, and wherein the impregnated or coated carrier is coated with a finely divided sorptive substrate and an acrylic polymer of a (1) hard, thermoplastic acrylic polymer having an intrinsic viscosity of from 0.75 dl/g to 3.1 dl/g at 30° C. in tetrahydrofuran, (2) hard, self-crosslinking thermoplastic acrylic polymers having an intrinsic viscosity of from 1.0 dl/g to 2.0 dl/g at 30° C. in dimethylformamide or (3) acrylic polymers having an intrinsic viscosity of from 0.05 dl/g to 0.1 dl/g at 30° C. in butanol, wherein the thus-obtained composition is characterized by decreased mammalian dermal toxicity and sustained pesticidal activity.

2. The composition according to claim 1 wherein the carrier is attapulgite or montmorillonite clays, brick chips, pumice, talc, volcanic cinders, corncob grits, sand or limestone chips in amounts ranging from 62% to 94% by weight of the overall composition; and when a sorptive carrier is selected, a deactivator selected from the group consisting of ethyl glycol, di-, tri- or tetraethylene glycol and mixtures thereof is incorporated in the compositions in amounts ranging from 3% to 6% by weight of total composition to neutralize the intrinsic acidity of the carrier, provided that the percent by weight amount is lowered with an amount equal to that of the deactivator employed; the pesticide being in amounts ranging from 2% to 25% by weight of the composition; and wherein the sorptive substrate is a calcined clay, diatomaceous earth, calcium silicate, fumed silica or fumed silica which has been made hydrophobic by replacement of most of the hydrophilic hydroxyl groups which populate the surface of the silica with trimethylsiloxyl groups in amounts ranging from 0.5% to 2% by weight of the total composition; the acrylic polymer being a hard, thermoplastic acrylic polymer having in intrinsic viscosity range of from 0.75 dl/g to 3.1 dl/g at 30° C. in tetrahydrofuran, a hard, self-crosslinking thermoplastic acrylic polymer having an intrinsic viscosity ranging from 1.0 dl/g to 2.0 dl/g at 30° C. in dimethylformamide or acrylic polymers having an intrinsic viscosity ranging from 0.05 dl/g to 0.1 dl/g at 30° C. in butanol in amounts ranging from 0.5% to 5% by weight of the total composition.

3. The composition according to claim 2 comprising 71.36% by weight of the montmorillonite clay; 15.19% by weight of 88.57% O,O-diethyl S-{[(1,1-dimethylethyl)thio]methyl}-phosphorodithioate; 3.63%, by weight of the ethylene di-, tri- and tetraethylene glycol deactivator mixture; coated with a hard, thermoplastic acrylic polymer latex, having an intrinsic viscosity ranging from 0.75 dl/g to 3.1 dl/g at 30° C. in tetrahydrofuran and the acrylic polymer latex comprises about 9.1% of the total composition.

4. The composition according to claim 2 comprising 75–77% by weight of the montmorillonite clay; 17.5% by weight of 88.57% O,O-diethyl S-{[(1,1-dimethylethyl)thio]methyl}phosphorodithioate; 4.0% by weight of the ethylene di-, tri- and tetraethylene glycol deactivator mixture; 0.5% by weight of fumed silica made hydrophobic by replacement of most of the hydrophilic hydroxyl groups populating the surface of the silica with trimethylsiloxyl groups; coated with a hard thermoplastic self-crosslinking acrylic polymer latex having an inrinsic viscosity of 1.4 dl/g at 30° C. in dimethylformamide and the acrylic polymer latex comprises about 1% to 3% by weight of the total composition.

5. The composition according to claim 2 comprising 7.36% by weight of the attapulgite clay; 15.91% by weight of 88.57% diethyl{S-[(1,1-dimethylethyl)thio]-methyl}phosphorodithioate; 3.63% by weight of the di- and triethylene glycol deactivator mixture; coated with a hard thermoplastic acrylic polymer latex having an intrinsic viscosity of from 0.75% dl/g to 3.1 dl/g at 30° C. in tetrahydrofuran and the acrylic polymer latex comprises about 9.1% by weight of the total composition.

6. The composition according to claim 2 comprising 75–77% by weight of the attapulgite clay; 17.5% by weight of 88.57% diethyl S-{[(1,1-dimethylethyl)thio]-methyl}phosphorodithioate; 4.0% by weight of the di- and triethylene glycol deactivator mixture; 0.5% by weight to 1.0% by weight of a fumed silica made hydrophobic by replacement of most of the hydrophilic hydroxyl groups populating the surface of the silica with trimethylsiloxyl groups; coated with a hard thermoplastic self-crosslinking acrylic polymer latex having an intrinsic viscosity of 1.4 dl/g at 30° C. in dimethylformamide and the acrylic polymer latex comprises about 1% to 3% by weight of the total composition.

7. The composition according to claim 2 comprising 79.07% by weight of the brick chips, 11.93% by weight of 88% O,O-diethyl S-(ethylthiomethyl)phosphorodithioate, 5% by weight of the diethylene glycol deactivator mixture; coated with a 37.5% solution of an acrylic polymer in tetrahydrofurfuryl alcohol wherein the acrylic polymer has an intrinsic viscosity of 0.085 dl/g at 30° C. in butanol and comprises about 4% by weight of the total composition.

8. A method for controlling the rate of toxicant release from a particulate composition containing the toxicant O,O-diethyl S-(ethylthio)methyl phosphorodithioate or O,O-diethyl S-{[(1,1-dimethylethyl)thio]methyl}phosphorodithioate comprising, applying to said particulate composition in amounts ranging from 0.5% to 5% by weight of the total composition an acrylic polymer of (1) hard, thermoplastic acrylic polymers having an intrinsic viscosity of from 0.75 dl/g to 3.1 dl/g at 30° C. in tetrahydrofuran, (2) hard self-crosslinking thermoplastic acrylic polymers having an intrinsic viscosity of from 1.0 dl/g to 2.0 dl/g at 30° C. in dimethylformamide, or (3) acrylic polymers having an intrinsic viscosity of from 0.05 dl/g to 0.1 dl/g in butanol and thereafter coating the acrylic polymer coated composition with a finely divided sorptive substrate; wherein the particulate composition comprises particles of an inert, course or finely divided sorptive or non-sorptive carrier impregnated or coated with a toxicant.

9. A method for controlling the rate of toxicant release from a particulate composition containing the toxicant O,O-diethyl S-(ethylthio)methylphosphorodithioate or O,O-diethyl S-{[(1,1-dimethylethyl)thio]methyl}phosphorodithioate comprising, coating said particulate composition with a finely divided sorptive substrate and thereafter applying to the coated composition in amounts ranging from 0.5% to 5% by weight of the total composition an acrylic polymer of (1) hard, thermoplastic acrylic polymers having an intrinsic viscosity of from 0.75 dl/g to 3.1 dl/g at 30° C. in tetrahydrofuran, (2) hard self-crosslinking thermoplastic acrylic polymers having an intrinsic viscosity of from 1.0 dl/g to 2.0 dl/g at 30° C. in dimethylformamide, or (3) acrylic polymers having an intrinsic viscosity of from 0.05 dl/g to 0.1 dl/g at 30° C. in butanol; wherein the particulate composition comprises particles of an inert, course or finely divided sorptive or non-sorptive carrier impregnated or coated with a toxicant.

* * * * *